United States Patent [19]

Chapman et al.

[11] Patent Number: 5,110,937

[45] Date of Patent: May 5, 1992

[54] PREPARATION OF DI-CATION ETHERS

[75] Inventors: Derek D. Chapman; Ronald R. Valente, both of Rochester, N.Y.

[73] Assignee: Eastman Kodak Company, Rochester, N.Y.

[21] Appl. No.: 400,844

[22] Filed: Aug. 30, 1989

[51] Int. Cl.$^5$ .............................. C07D 401/12
[52] U.S. Cl. ................................. 546/261
[58] Field of Search ....................... 546/261

[56] References Cited

U.S. PATENT DOCUMENTS

| | | | |
|---|---|---|---|
| 4,043,819 | 8/1977 | Baumann | 430/283 |
| 4,440,773 | 4/1984 | Crossley et al. | 546/261 |
| 4,734,350 | 3/1988 | Lin et al. | 428/404 |

FOREIGN PATENT DOCUMENTS 822871 11/1959 United Kingdom .

OTHER PUBLICATIONS

Strang et al., J. Am. Chem. Soc., 103, pp. 4837–4845 (1981).
Villiers et al., Rec. Trav. Chim., 76, pp. 647–656 (1957).
Renger, Synthesis, Sept. 1985, pp. 856–860.
Hopkins et al., J. Org. Chem., 32, pp. 4040–4044 (1967).
Pirzada et al., CA 84:105364j.
Stang et al. CA 93:203397c.

Primary Examiner—Jane T. Fan
Attorney, Agent, or Firm—Robert A. Linn

[57] ABSTRACT

Di-cation ether salts are prepared by a reaction sequence which comprises
(i) N-alkylating a 2-halopyridine,
(ii) reacting the N-alkylated product with a 2-hydroxypyridine in the presence of sufficient organic base to combine with the by-product hydrohalic acid, and
(iii) reacting the mono-cation ether thereby produced with an alkylating agent.

The process is conducted in the presence of a solvent, such as acetonitrile. The di-cation can be isolated by removal of the solvent, followed by contacting the reaction mixture with an aqueous fluoborate, whereby the di-cation ether precipitates as the fluoborate salt. The di-cation ether is prepared in surprisingly high yield. The process can be conducted in one reaction vessel without isolation of a product intermediate formed in the reaction sequence. The fluoborate product is quite pure. If desired, the fluoborate anion can be removed from the di-cation ether by suspending the di-cation ether fluoborate in water, and reacting it with a potassium salt such as $KNO_3$. The soluble di-cation product thereby produced can be used as a gelatin hardener, or as a chemical intermediate.

11 Claims, No Drawings

PREPARATION OF DI-CATION ETHERS

FIELD OF THE INVENTION

This invention relates to the preparation of di-cation ethers, more particularly to di-cation ether salts. In a particular embodiment, this invention relates to the preparation of bis(1-methyl-2-pyridinium)ether difluoborate, also known as 1,1'-dimethyl-2,2'-oxydipyridinium difluoborate. In a highly preferred embodiment, such a salt is prepared by a sequential process, in a batch operation in a single reaction vessel, using a 2-halopyridine and 2-hydroxypyridine as starting materials, and without isolation of a reaction intermediate.

BACKGROUND OF THE INVENTION

Di-cation ether salts have been prepared by a method described by Stang et al in a reference cited below. As pointed out by the authors, the di-cation ethers are the first known bis(carbenium ions). The Stang et al method for forming the ethers comprises reaction of non-enolizable activated ketones with trifluoromethanesulfonic ("triflic") anhydride. The cost of triflic anhydride is substantial; therefore, its use is not preferred in large-scale commercial synthesis.

Another method of producing di-cation ethers comprises the alkylation of an ether such as 2,2'-bis(pyridyl) ether. Such ethers can be prepared by the silver salt method described in DeVilliers et al, *Rec. Trav. Chim.*, 76, 647, 1957. The use of silver entails significant expense. Moreover, the method of DeVilliers et al does not form 2,2'-bis(pyridyl) ethers in high yield. In other words, when the method of DeVilliers et al is employed, the desired 2,2'-bis(pyridyl) ether is produced with an undesirable amount of a pyridone such as N-(2'-pyridyl)-2-pyridone:

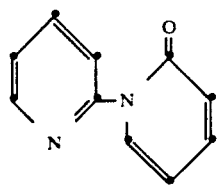

Consequently, the DeVilliers method does not lend itself to a commercially viable reaction sequence for the production of 2,2'-oxydipyridinium salts.

When the silver salt of the Villiers process is replaced by the analogous sodium salt, the pyridone is produced in even greater excess over the bis(pyridyl) ether. Thus, the bis(pyridyl) ethers are not preferred for large-scale commercial production.

From the work of Hopkins et al on the alkylation of 2-hydroxypyridine (paper cited below), it is known that the product composition is very dependent on the nature of the alkylating agent, the nature of the acid acceptor, and the solvent. Generally, it is known to employ the silver salt to obtain O-alkylation, and that even then some N-alkylation is observed. As indicated above, use of silver salts is not preferred for commercial preparation.

Applicants' method for the synthesis of di-cation ethers comprises the reaction of a 1-alkyl-2-halopyridinium salt with 2-hydroxypyridine in the presence of a tertiary organic base. It will be apparent to the skilled practitioner that with such reactants there is a possibility of reaction at the nitrogen as well as at the oxygen of the hydroxypyridine anion. Furthermore Applicants do not employ a silver salt as suggested by the art. Consequently it was therefore surprising that Applicants' method gives good yields of a desired oxygen-reacted product (which can be converted into a 2,2'-oxydipyridinium salt). The preparation of di-cation ethers and their use as hardeners is disclosed in Chen et al application Ser. No. 238,665, filed Aug. 31, 1988, and now allowed.

RELATED ART

Stang et al, *J. Am. Chem. Soc.*, 103, 4837–4845 (1981) discloses a preparation of di-cation ether salts. The method comprises the reaction of an activated non-enolizable ketone with triflic anhydride.

Villiers et al, *Rec. Trav. Chim.*, 76, 647 (1957) discloses a method involving a silver salt which prepares a poor yield of 2,2'-bispyridyl ether. Use of a sodium salt is referred to on page 649.

Hopkins et al, *J. Org. Chem.*, 32, 4040-4 (1967) reports a study of the reaction of alkali metal and silver salts of 2-pyridone with alkyl halides and tosylates in a variety of solvents. The ratios of nitrogen to oxygen alkylation were quantitatively determined.

SUMMARY OF THE INVENTION

The heart of this invention comprises the discovery that a 1-alkyl-2-halopyridinium salts will react with a 2-hydroxypyridine to form an ether in high yield. This invention also comprises the discovery that this reaction will take place in high yield when the 1-alkyl-2-halopyridinium salt is employed in a reaction mixture prepared by reacting a 2-halopyridine and a suitable alkylating agent. This invention also comprises the discovery that the aforementioned reactions can be used in an elegant sequential method for preparing di-cation ethers. Furthermore, this invention provides a reaction sequence for preparing a di-cation ether in high yield in a batch process conducted in one reaction vessel without isolating an intermediate for the di-cation ether. Moreover, in this invention, the di-cation ether can be isolated in high purity (from the reaction mixture in which it is produced) by precipitation from an aqueous solution of fluoborate.

Di-cation ethers, such as those formed by the process of this invention, can be used to harden gelatin. Furthermore, they can be used as starting materials for preparing other chemical products; cf Stang et al, supra, page 4841.

DESCRIPTION OF PREFERRED EMBODIMENTS

In one aspect, this invention comprises a reaction sequence for preparing di-cation ethers. Thus, this invention comprises a process for the preparation of a salt of a di-cation ether having the formula:

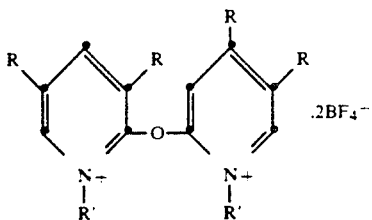

wherein each substituent designated by R is independently selected from the class consisting of hydrogen, halogen, and alkyl radicals having up to about four carbon atoms, such that not more than one halogen is bonded to either ring, and said each radical designated by R' is selected from alkyl radicals having up to about four carbon atoms, said process comprising the stepwise reaction sequence of:

(A) reacting (i) an alkylating agent selected from the class consisting of dimethylsulfate, diethylsulfate, alkyltoluene sulfonates, and compounds having the formula R'OSO$_2$CF$_3$, wherein R' has the same significance as above, with (ii) a halopyridine having the formula:

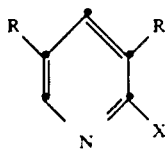

wherein R has the same significance as above and X is halogen having an atomic number of at least 17, (B) reacting in the presence of a tertiary alkyl amine, the N-alkylated intermediate product of step (A) with a hydroxypyridine having the formula:

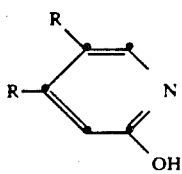

wherein R has the same significance as above, and not more than one R is halogen, (C) reacting the mono N-alkylated ether intermediate thereby produced with an alkylating agent selected from the class of alkylating agents set forth above, and (D) reacting the di-N-alkylated ether intermediate thereby produced with a water soluble metal fluoborate whereby said di-cation ether salt of Formula (I) is produced;

said process being further characterized by having a yield of said di-cation ether salt in substantial excess of any yield of a pyridone co-product. For the purpose of this invention when "substantial excess" is used in this sense, it means there is about 10 times as much pyridyl ether formed than pyridone by-product.

As pointed out above, Step (A) comprises the reaction of an alkylating agent and a 2-halopyridine. The 2-halopyridine employed does not have substituents which prevent the alkylation of the nitrogen atom from taking place. Generally speaking, it is preferred to employ 2-halopyridine where the 4-position, and the 6-position are unsubstituted. Of the substituents in the 3-position and 5-position, i.e., meta to the ring nitrogen atom, it is preferred that they be selected from substituents which (i) are stable under the reaction conditions employed, (ii) do not cause an undesirable side reaction to take place to an appreciable extent, or (iii) otherwise interfere with the course of the reactions employed in the process of this invention. For the purpose of this invention, such substituents are designated "inert" substituents. Preferred inert substituents include hydrogen and lower alkyl groups, e.g., methyl, ethyl, n-propyl, sec-butyl, n-pentyl, and the like. More preferably, the alkyl radicals have up to about four carbon atoms. Preferred inert substituents also include halogens, more preferably chlorine, bromine, and iodine, most preferably chlorine and bromine. Substituent X in Formula (I) is also selected from the halogens mentioned in this paragraph. A preferred reactant is 2-chloropyridine.

With regard to the alkylating agent employed in Step (A), one employs an agent capable of alkylating the ring nitrogen atom in the 2-halopyridine. Such alkylating agents are exemplified by the alkylating agents which were mentioned above. Of these, dimethylsulfate, diethylsulfate, CH$_3$OSO$_2$CF$_3$, and C$_2$H$_5$OSO$_2$CF$_3$ are preferred. For commercial scale production the alkyl sulfates are more preferred.

For Step (B), one may employ the N-alkylated compound in the reaction mixture produced by Step (A). Alternatively, one may employ a preformed 1-alkyl-2-halopyridinium compound. If a preformed pyridinium compound is employed, the counter ion is selected from anions which will not interfere with the process step(s) employed in this invention. Such counter ions can be selected from those conferred by the aforementioned alkylating agents, and sulfate, chloride, bromide, toluenesulfonate, methanesulfonate, and the like.

In Step (B) a hydroxypyridine compound having Formula (III) is employed. It is preferred that the substituents on the hydroxypyridine be identical in type and position to the substituents on the starting 2-halopyridine (or the preformed 1-alkyl-2-halopyridinium cation) so that the product di-cation will be symmetrical. However, this is not critical; and this invention includes the preparation of unsymmetrical products. Stated another way, it is preferred that the R in the 4-position of the 2-hydroxypyridine is hydrogen, but compounds in which the 4-position has other substituents can be employed. In Formula (III) each R has the same significance as the R in Formula (II). Hence, in a preferred embodiment, each R in Formula (III) is selected from the preferred inert substituents set forth above where the 2-halopyridine is discussed. A preferred reactant is 2-hydroxypyridine, which is also referred to in the literature as 2-pyridone. In the product of Step (B) the counterion is the anion present in the 1-alkyl-2-halopyridinium salt. Such counterions are mentioned above.

Step (B) is conducted in the presence of an organic base to combine with the by-product acid that is formed, and thereby assist in driving the reaction toward completion. Any organic base that does not interfere with the process can be used. Preferably the base is an aliphatic tertiary amine having three alkyl groups bonded to nitrogen. Preferably, the three alkyl groups are the same, and they are selected from alkyl groups having from two to about six carbon atoms. Triethylamine is a preferred tertiary amine. Generally, enough base is used to react with all of the acid that will be liberated by the reaction of step (II). Large excesses of base may unnecessarily introduce complications into the process, and they are therefore not preferred. In general, a substantially stoichoimetric amount of an organic base is employed. For the purposes of this invention "substantially stoichiometric" encompasses a stoichiometric amount, as well as amounts that are slight departures from stoichiometric, for example, the departures introduced by inadvertent weighing errors. Generally speaking, "substantially stoichiometric" means stoichiometric ±0.05 moles.

In Step (B), the salt of the base that is formed is not soluble in the reaction mixture. It is removed from the reaction zone, preferably before conducting Step (C). The salt is conveniently removed by filtration.

In Step (C), the mono cationic ether product of Step (B) is reacted with an alkylating agent to form the desired di-cation. The alkylating agent used for this purpose is preferably selected from the same class of alkylating agents as used in Step (A). Preferably, the alkylating agent is selected so that the alkyl groups bonded to both nitrogens in the di-cation are the same. More preferably, both alkyl groups are methyl or ethyl, most preferably methyl.

After the alkylation in Step (C), the reaction mixture is concentrated by removal of substantially all of the solvent that is present. This can be accomplished by distillation, preferably under somewhat reduced pressure, for example, at about 20 mm Hg. The solvent removal facilitates the reaction of the di-cation product of Step (C) with the aqueous metal fluoborate solution used in Step (D).

Step (D) is conducted to separate the di-cation from the mixture containing it. For this step, an aqueous solution of a metal fluoborate is employed. Any metal fluoborate which is sufficiently soluble in water can be used. Sodium fluoborate is a preferred reactant; the use of lithium fluoborate is also suggested. A fairly concentrated solution of the fluoborate in water is preferred. In general, it is preferred to use a solution of sodium fluoborate having a concentration of from about 460 to about 500 grams per liter.

The di-cation product is precipitated by the process of Step (D) and can be recovered by filtration. It can be washed to further purify it if desired. If the fluoborate salt of the di-cation is not desired, the precipitate of Step (D) can be resuspended in water and reacted with a potassium salt having the desired cation. The potassium fluoborate which is formed is insoluble to an appreciable extent in water and can be filtered off, leaving an aqueous mixture of the desired di-cation salt. For example, the di-cation fluoborate can be resuspended in water and reacted with potassium nitrate to form the di-cation dinitrate. This material can be used to harden gelatin or as a chemical intermediate.

The steps for forming the di-cation ether in the above-described reaction sequence are conducted in the presence of a solvent. A suitable solvent for this process (i) has the ability to dissolve the reactants and desired products, (ii) does not react with them to an untoward extent, and (iii) does not favor N-alkylation, to a significant extent. Preferred solvents have a high enough boiling point to enable the reactions to be conducted at temperature(s) which give good reaction rates, without the need to resort to superatmospheric pressures. A preferred solvent is acetonitrile. Other solvents having the above characteristics can be used if desired.

The amount of solvent is not critical. One uses enough solvent to dissolve the materials which the operator wishes to remain in solution. There is no real upper limit on the amount of solvent employed, this being governed by such secondary considerations as the size of the reaction vessel, process economics, the ease of separation of product, etc. In general, one employs about two parts by weight of solvent per each one part by weight of chloropyridine. More solvent can be added (e.g., with an organic base) so that the total amount of solvent is about four times by weight the amount of 2-chloropyridine. Greater or lesser amounts can be used if desired.

In the sequential process of this invention, Steps (A), (B), and (C) as defined above are conveniently carried out in acetonitrile at reflux temperature. It is not necessary to conduct the aforementioned reaction steps at this temperature; higher or lower temperatures can be used if desired. Typically, the operator selects a temperature which gives a reasonable rate of reaction, and which does not cause an intolerable amount of decomposition of one or more materials in the reaction zone. In general, the higher the temperature, the faster the rate of reaction. Thus, for example, Steps (A)–(C) can be conducted at temperatures within the range of from about 60° to about 100° C., or higher. If the reaction temperature selected is above the normal boiling point of acetonitrile (~82° C.), the reaction can be conducted at a superatmospheric pressure sufficient to allow the desired temperature to be reached.

Although the processes of this invention can be conducted at subatmospheric pressures, and as explained above at superatmospheric pressures, ambient pressure is preferred.

For the sequential process described above, the reactants of Steps (A) and (B) are employed in substantially molar equivalent amount. In other words, it is preferred that the reactants be employed in stoichiometric amounts, or in amounts which are slight departures from stoichiometric, as defined above.

In Step (C) one may use stoichiometric or substantially stoichiometric quantities, or an excess of the alkylating agent, as an aid in driving the reaction to completion. Thus in Step (C), one may use a 10% or larger excess of alkylating agent. It is preferred that the amount of alkylating agent be from 1.0 to 1.1 times the amount of other reactant.

In Step (D), it is preferred that the soluble fluoborate be employed in substantially stoichiometric amount. Lesser amounts of fluoborate cause di-cation ether to remain in solution and thereby reduce product recovery.

Use of the materials in the above-discussed amounts conserves starting materials and simplifies product workup. If these items are not of importance to the operator, greater excesses of one or more reactants can be employed.

When calculating the weight of materials to be employed in Steps (B)–(D), an operator can assume that the previous reactions occurred in 100% yield if the reactants in previous steps were employed in substantially stoichiometric amounts. A skilled practitioner can also follow the course of the reaction(s) by NMR or thin layer chromatography (TLC) or similar technique, and use the data obtained to determine the amounts of reactants to be employed.

The reaction times for Steps (A)–(C) are not truly independent variables, but are dependent to at least some extent on the other reaction conditions employed (e.g., reaction temperature), the inherent reactivity of the reactants, etc. In general one may use reaction times within the following ranges:
Step (A)—1–24 hours
Step (B)—2–8 hours
Step (C)—10–24 hours
The reaction time for Step (D) is dependent at least to some extent on the rate of addition of the soluble fluoborate to the reaction zone. It can usually be completed in from about one minute to about one hour. In some instances it is desirable to let the reaction mixture stand for about 0.5–1.0 hour to allow the product to precipitate. It is to be understood that reaction times outside one of the above ranges can be used if desired. Ambient temperature and pressures are conveniently employed. One may use the reaction temperature conferred by fluoborate solution made with the process water available at the reaction site.

Recovery of the di-cation ether by precipitation as the difluoborate salt is a preferred embodiment of this invention. However, the invention is not limited to this method of isolation. Thus, this invention comprises isolation of the di-cation ether by any method known to one skilled in the art. For example, the di-cation ether can be recovered as a salt other than a difluoborate which is relatively insoluble in water. Thus, one can recover the di-cation ether as a hexafluoro phosphate, or as a similar salt.

Moreover, the di-cation ether product may be recovered as a salt containing a counterion Y, such as those mentioned above when discussing step (B), by adding a liquid to the reaction mixture resulting from step (C) to precipitate the product of that step from solution. Preferably such a liquid is miscible with acetonitrile (or other reaction solvent) and is a poor solvent for the di-cation ether product formed by step (C).

The following examples illustrate the process of this invention.

EXAMPLE 1

Preparation of 1,1'-Dimethyl-2,2'-Oxypyridinium Difluoborate

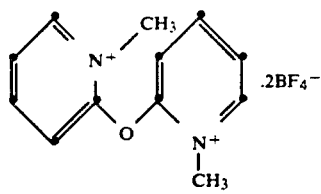

2-Chloropyridine (11.3 g) was dissolved in acetonitrile (20 ml) and dimethyl sulfate (13.5 g) added. The reaction mixture was refluxed for 16 hours and then cooled. 2-Hydroxypyridine (9.6 g) was added followed by triethylamine (10.2 g) dissolved in acetonitrile (30 ml). The reaction mixture was refluxed for four hours and cooled. Triethylamine hydrochloride was removed by filtration and dimethyl sulfate (13.5 g) added to the filtrate. The mixture was refluxed overnight (ca 15 hours) and concentrated to dryness. Sodium fluoborate (23 g) was dissolved in water and the solution filtered to remove some insoluble material. The filtrate was added to the residue and stirred vigorously. The product precipitated and was filtered off and washed with ethanol and ether. Yield 22.5 g.
NMR 4.35 (s 6 protons), 8.02–9.15 ppm (m 8 protons).

EXAMPLE 2

Preparation of 1-Ethyl-1'-Methyl-2,2'-Oxydipyridinium Difluoborate

2-Chloropyridine (5.7 g) and ethyl trifluoromethanesulfonate (8 g) were mixed in acetonitrile (15 ml) and the solution refluxed gently for 30 minutes. After the solution was cooled, 2-hydroxypyridine (4.8 g) and triethylamine (5.1 g) were added and the mixture refluxed for six hours. The solution was then cooled and filtered to remove triethylamine hydrochloride. Dimethyl sulfate (6.8 g) was added to the filtrate and the solution refluxed overnight. After evaporation of the solvent, a filtered solution of sodium fluoborate (14 g) in water (50 ml) was added. The product was isolated by the addition of ethanol.

Yield 10 g: 51%; Anal: Found: C, 40.46; H, 4.15; N, 7.17. Calcd. for $C_{13}H_{16}B_2F_8N_2O$: C, 40.05; H, 4.14; N, 7.18. NMR 1.54 (s 3 protons), 4.32 (s 3 protons), 4.73 (q 2 protons) 8.02–9.13 ppm (m 8 protons).

EXAMPLE 3

Large Scale Preparation of 1,1'-Dimethyl-2,2'-Oxydipyridinium Difluoborate

| Starting Materials | Amount |
| --- | --- |
| Acetonitrile | 70.7 kg |
| Triethylamine | 11.9 kg |
| Dimethyl Sulfate | 31.2 kg |
| 2-Chloropyridine | 12.75 kg |
| Sodium Fluoborate | 27.15 kg |
| 2-Hydroxypyridine | 11.2 kg |

Process Equipment 50-gallon glass-lined vessel, equipped with variable speed, stirrer, and heating and cooling means
Stainless steel filter box
Vacuum oven
All equipment is to be cleaned with hot water followed by acetone under a nitrogen purge.

Process Description

1. Place a clean, dry, 50-gallon, glass-lined vessel under partial vacuum (~100–300 Torr).
2. Add to the vessel 21.9 kg of acetonitrile.
3. Add to the vessel 12.75 kg (112.35) moles of 2-chloropyridine.
4. Activate the stirrer.
5. Heat the reaction solution to 60° C.
6. Add to the vessel 15.6 kg (123.6 moles) of dimethyl sulfate over a 30-minute period. Maintain the reaction temperature at 65° C. using necessary cooling.
7. Heat the reaction mixture to reflux (82° C.) and maintain reflux for two hours. Check for completion by thin layer chromatography (TLC). The 2-chloropyridine should disappear.
8. Cool the reaction to room temperature (RT).
9. Add to the vessel 11.2 kg (117.9 moles) of 2-hydroxypyridine.
10. In a second 50-gallon vessel prepare a solution of 11.9 kg (117.9 moles) of triethylamine and 30.8 kg of acetonitrile.

11. Add the triethylamine solution to the reaction mixture. Keep the reaction temperature below 50° C. using cooling and controlling the addition rate. The reaction mixture will darken.
12. Heat the reaction mixture to reflux (82° C.) and maintain reflux for two hours. Check for completion by TLC. The 2-hydroxypyridine should disappear.
13. Cool the reaction mixture to RT.
14. Filter the product liquors to a clean, 50-gallon, glass-lined vessel.
15. Slurry the triethylamine hydrochloride residues with 18 kg of acetonitrile (3×'s 6 kg). Filter the acetonitrile wash to the second vessel.
16. Dispose of the triethylamine hydrochloride residues.
17. Add to the product solution 15.6 kg (123.45 moles) of dimethyl sulfate.
18. Heat the reaction to reflux (82° C.) and maintain reflux for 16 hours (overnight). Check for completion by TLC.
19. Carefully place the vessel under full vacuum and concentrate the reaction mixture to ⅓ volume (Stirring will be necessary. The mixture will get thick).
20. In a second clean, 50-gallon vessel, make up a solution of 27.15 kg (247.17 moles) of sodium tetrafluoroborate and 18 gallons of water. Stir at RT one hour. This is about the maximum solubility of sodium tetrafluoroborate in water at RT. Filter out any insolubles.
21. While stirring the concentrated product mixture, add the sodium tetrafluoroborate solution. Do not allow the temperature to exceed 30° C. during the addition.
22. Stir at RT for one hour allowing the product to precipitate.
23. Drop the product slurry to a grounded stainless steel filter box.
24. Wash the product cake with 18 kg of isopropyl alcohol.
25. Place the damp solids on trays and dry in a 40° C. vacuum oven to <=1.0% volatiles.
26. The expected yield is 23.7 kg to which is 54% of theory.

EXAMPLE 4

Preparation of
1,5-Dimethyl-1'-Methyl-2,2'-Oxydipyridinium Difluoborate

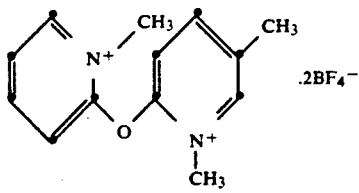

2-Bromo-5-methylpyridine (8.6 g) and dimethyl sulfate (6.8 g) were added to acetonitrile (20 ml) and the solution refluxed overnight. After cooling, 2-hydroxypyridine (4.8 g) and triethylamine (5 g) were added and the mixture refluxed for six hours. After cooling, dimethyl sulfate (6.8 g) was added and the solution refluxed overnight. The reaction was worked up by evaporation to dryness and adding a filtered solution of sodium fluoborate (14 g) in water (50 ml). The product was isolated by precipitation with ethanol.

Yield 7.7 g; 40%; Anal: Found: C, 39.55; H, 3.99; N, 7.07. Calcd. for $C_{13}H_{16}B_2F_8N_2O$: C, 40.05; H, 4.14; N, 7.18%. NMR 2.45 (s 3 protons), 4.31 (s 6 protons), 7.95–9.05 ppm (m 7 protons).

The procedures of the above Examples can be repeated with the other reactants of Formulas II and III using a reaction temperature within the range of from about 60° C. to about 100° C. in Steps (A)–(C), and a reaction temperature within the range of from about 10° C. to about 30° C. for Step (D). The procedure can be employed using any of the alkylating agents and tertiary alkyl amines discussed above.

The di-cation ethers of Formula (I) produced by the process of this invention can be used to harden any type of gelatin. Types of gelatin useful in the practice of the present invention include alkali-treated gelatin, acid-treated gelatin, partially phthalated gelatin, double-dipped gelatin (i.e., gelatin treated with both alkali and acid), and the like.

The di-cation ethers of Formula (I) provide rapid hardening of gelatin with little or no after-hardening while avoiding many of the adverse photographic effects found with prior art hardeners, such as speed loss and fog. The hardening compounds of formula (I) also are not highly hygroscopic as are many prior art hardening compounds, making them easy to handle. Additionally, the gelatin hardened according to the invention exhibits desirable physical properties, such as low tackiness.

Gelatin is hardened by combining it with a hardening compound having a di-cation ether of Formula (I). This is accomplished by techniques known to those skilled in the art. For example, the aqueous solution of the hardening compound can be applied directly to an unhardened gelatin layer that has been coated on a support. Alternatively, the hardening compound can be mixed with the composition to be hardened shortly before coating it onto a support. Another method is to coat the compound in a gelatin or non-gelatin (e.g., synthetic polymer) layer as an overcoat or as an internal layer of a photographic element in a manner such that it will diffuse into other layers of the element to harden those other layers.

The di-cation ethers can also be used to partially harden gelatin. This is done, for example, by increasing the chain length of the gelatin, as described in U.S. Pat. No. 4,421,847.

The amount of hardener used to harden gelatin according to the present invention will vary according to the purpose for which the gelatin is being used, the degree of hardening desired, and the particular compound used. If only a slight amount of hardening is desired, relatively small amounts of hardening compound can be used. If a greater degree of hardening is desired, relatively large amounts of hardener would be used. The amount of hardener used according to the present invention is preferably between 0.01 and 20 weight percent, based on the weight of dry gelatin, and more preferably between 0.05 and 10 weight percent, based on the weight of dry gelatin.

The invention has been described in detail above with particular reference to preferred embodiments. A skill practitioner familiar with the above-detailed description can make many changes and substitutions without departing from the scope and spirit of the claims which follow.

We claim:

1. Process for the preparation of a salt of a di-cation ether having the formula:

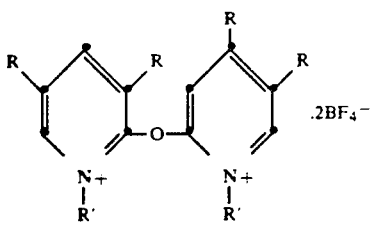

wherein each substituent designated by R is independently selected from the class consisting of hydrogen, halogen, and lower alkyl radicals, such that not more than one halogen is bonded to either ring, and said each radical designated by R' is lower alkyl radicals, said process comprising the stepwise reaction sequence of:

(A) reacting (i) a halopyridine having the formula

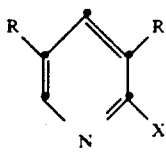

wherein R has the same significance as above and X is halogen having an atomic number of at least 17, with (ii) an alkylating agent selected from the class consisting of dimethylsulfate, diethylsulfate, alkyltoluene sulfonates, and compounds having the formula $R'OSO_2CF_3$, thereby N-alkylating said halopyridine, (B) reacting in the presence of a tertiary alkyl amine, the N-alkylated intermediate product of step (A) with a hydroxypyridine having the formula:

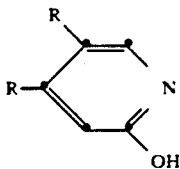

wherein R has the same significance as above, and not more than one R is halogen;

(C) reacting the mono N-alkylated ether intermediate thereby produced with an alkylating agent selected from the class of alkylating agents set forth above; and (D) reacting the di-N-alkylated ether intermediate thereby produced with a water soluble metal fluoborate whereby said di-cation ether salt of Formula (I) is produced; said process being further characterized by having a yield of a di-cation ether salt in substantial excess of any yield of a pyridone co-product.

2. A process according to claim 1, wherein steps (A), (B), and (C) are conducted in the presence of acetonitrile as a solvent, and a salt of said tertiary alkyl amine is removed prior to conducting step (C).

3. A process according to claim 2, wherein said acetonitrile is substantially removed from the reaction mixture produced by step (C) prior to conducting step (D), and step (D) is conducted by adding an aqueous solution of said metal fluoborate, whereby said di-cation ether salt is precipitated.

4. A process according to claim 3 wherein the reactants of steps (A) and (B) are employed in substantially molar equivalent amount, and in step (C) the amount of said alkylating agent employed therein is from about 1.0 to about 1.1 times the molar equivalent amount of said mono-N-alkylated ether product of step (B).

5. The process of claim 4 being conducted in one reaction vessel without isolation of any of said intermediate products.

6. A process for the preparation of the di-cation ether salt, said process comprising the sequence of:

(A) reacting 2-chloropyridine and dimethyl sulfate in acetonitrile solvent to prepare an N-methylpyridinium intermediate, (B) reacting 2-hydroxypyridine with said intermediate in the reaction mixture produced by step (A), and in the presence of a tertiary alkyl amine added thereto, (C) removing a salt of said tertiary alkyl amine from the reaction mixture produced in step (B), (D) reacting the mono N-alkylated ether in the substantially salt-free reaction mixture thereby produced with dimethyl sulfate, (E) removing substantially all of said acetonitrile from the reaction mixture thereby produced, (F) reacting sodium fluoborate in water and the di-N-alkylated ether product of step (D), whereby said 1,1'-dimethyl-2,2'-oxydipyridinium difluoborate product is precipitated;

said process being further characterized by being conducted in one reaction vessel without removal of an intermediate to said product; said process being further characterized by having a yield of a di-cation ether salt in substantial excess of any yield of a pyridone Co-Product.

7. A process according to claim 6 wherein said tertiary alkyl amine is triethyl amine.

8. A process for the preparation of an ether having the formula:

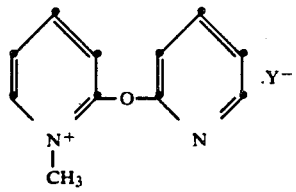

said process comprising reacting 1-methyl-2-halopyridinium salt with 2-hydroxypyridine in the presence of a tertiary alkyl amine sump for by-product HCl, and in the presence of a solvent quantity of acetonitrile; said process being conducted at a temperature within the range of from about 70° C. to about 90° C.

9. A process according to claim 8 wherein said halopyridine is 2-chloropyridine.

10. A process according to claim 9 conducted at reflux at ambient pressure.

11. Process for the preparation of a di-cation ether having the formula:

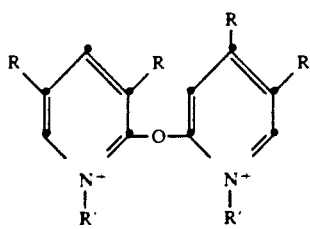

(I)

wherein each substituent designated by R is independently selected from the class consisting of hydrogen, halogen, and lower alkyl radicals, such that not more than one halogen is bonded to either ring, and said each radical designated by R' is lower alkyl radicals, said process comprising the stepwise reaction sequence of:

(A) reacting (i) an alkylating agent selected from the class consisting of dimethylsulfate, diethylsulfate, alkyltoluene sulfonates, and compounds having the formula $R'OSO_2CF_3$, with (ii) a halopyridine having the formula:

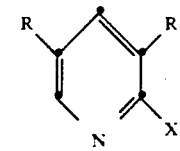

(II)

wherein R has the same significance as above and X is halogen having an atomic number of at least 17, (B) reacting in the presence of a tertiary alkyl amine, the N-alkylated intermediate product of step (A) with a hydroxypyridine having the formula:

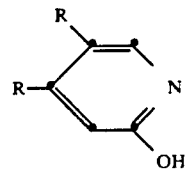

(III)

wherein R has the same significance as above, and not more than one R is halogen, and (C) reacting the mono N-alkylated ether intermediate thereby produced with an alkylating agent selected from the class of alkylating agents set forth above; said process being further characterized by having a yield of a di-cation ether salt in substantial excess of any yield of a pyridone co-product.

* * * * *